US00PP24275P3

(12) United States Plant Patent
Randag

(10) Patent No.: US PP24,275 P3
(45) Date of Patent: Feb. 25, 2014

(54) VARIETY OF CALLA LILY NAMED 'CALGARY'

(50) Latin Name: *Zantedeschia sprengeri*
Varietal Denomination: Calgary

(75) Inventor: Cecilius Jan-Jochem Randag, Bosweg (NL)

(73) Assignee: Sande B.V., 't Zand (NL)

( * ) Notice: Subject to any disclaimer, the term of this patent is extended or adjusted under 35 U.S.C. 154(b) by 0 days.

(21) Appl. No.: 13/374,388

(22) Filed: Dec. 27, 2011

(65) Prior Publication Data

US 2013/0167277 P1 Jun. 27, 2013

(51) Int. Cl.
*A01H 5/00* (2006.01)

(52) U.S. Cl.
USPC ..... Plt./490

(58) Field of Classification Search
USPC ..... Plt./490
See application file for complete search history.

*Primary Examiner* — Kent L Bell
(74) *Attorney, Agent, or Firm* — The Webb Law Firm

(57) ABSTRACT

'Calgary' is a new variety of calla lily having inflorescences with a creamy-colored spathe that produces 3-20 inflorescences per tuber. The inflorescence stems are about 25 cm. in height and the leaves are green with whitish spots and have a leathery texture. The new variety has a dwarf plant architecture.

4 Drawing Sheets

Botanical classification: *Zantedeschia sprengeri.*
Varietal denomination: 'CALGARY'.

BACKGROUND OF THE NEW PLANT

The present invention comprises a new and distinct cultivar of calla lily, botanically known as *Zantedeschia sprengeri* and hereinafter referred to by the cultivar name 'Calgary'.

'Calgary' is a product of a planned breeding program which had the objective of creating *Zantedeschia* hybrids for pot flower production in a wide range of colors with a large, classic inflorescence shape. The breeding program began in 1989 and the new cultivar is a seedling selected from the crossing of *Zantedeschia sprengeri* seedling Z981074 (female parent, unpatented) with *Zantedeschia sprengeri* seedling Z010437 (male parent, unpatented). 'Calgary' was selected in 2007 by the inventor C. J. J. Randag in 't Zand, The Netherlands as one flowering plant within the progeny of the stated cross.

The first act of asexual reproduction of 'Calgary' by tissue culture was performed by the inventor in September of 2007 in 't Zand, The Netherlands. Further asexual reproductions by tissue culture at the same location has demonstrated that the combination of characteristics as herein disclosed for the new cultivar are retained and reproduced true to type through successive generations of asexual reproduction.

The following observations, measurements and comparisons describe plants grown in 14 cm. pots in 't Zand, The Netherlands under greenhouse conditions which approximate those generally used in horticultural practice. Color references are made to The R.H.S. Colour Chart of The Royal Horticultural Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Calgary' which, in combination, distinguish this calla lily as a new and distinct cultivar:

1. Creamy-colored spathe;
2. Dwarf-like growth habit; and
3. High inflorescence production.

Table 1 provides similarities and differences of 'Calgary' to its parents and 'Chrystal Blush' (unpatented).

TABLE 1

| 'Calgary' | Similarities | Differences |
|---|---|---|
| Z981074 | Leaf shape | Color of spathe<br>Plant height |
| Z010437 | Spathe shape | Number of spathes<br>Color of spathe<br>Color of spadix |
| 'Chrystal Blush' | Leaf shape | Color of spadix<br>Plant height<br>Spots in leaves |

BRIEF DESCRIPTION OF THE DRAWINGS

The accompanying photographic drawings illustrate the new variety, with the colors being as nearly true as is possible with color illustrations of this type.

DESCRIPTION OF THE PLANT

The Plant

Figure 1:
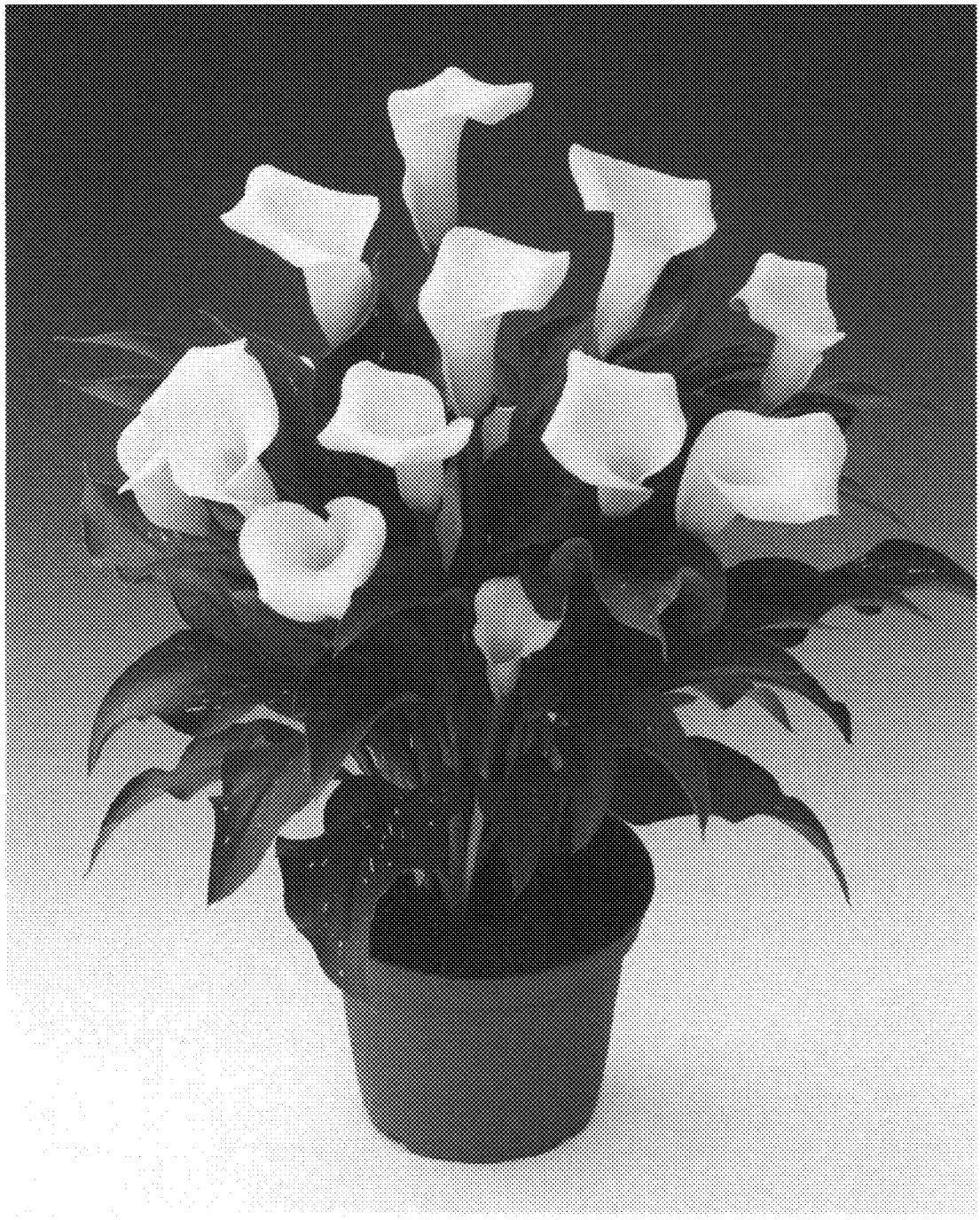
FIG. 1 is a photograph of an entire plant of the new variety.
Figure 2:
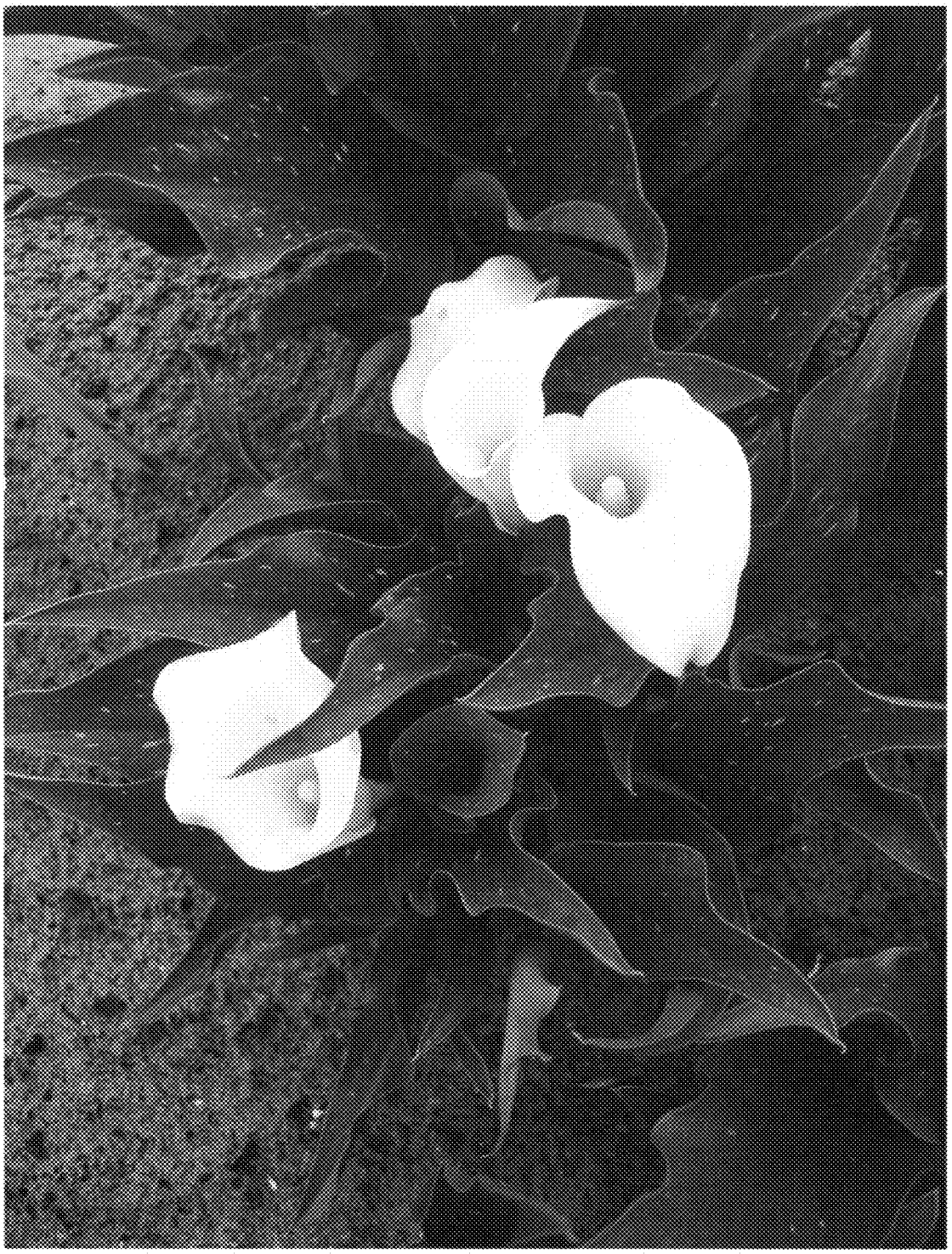
FIG. 2 is a photograph of an overhead view of the new variety.
Figure 3:
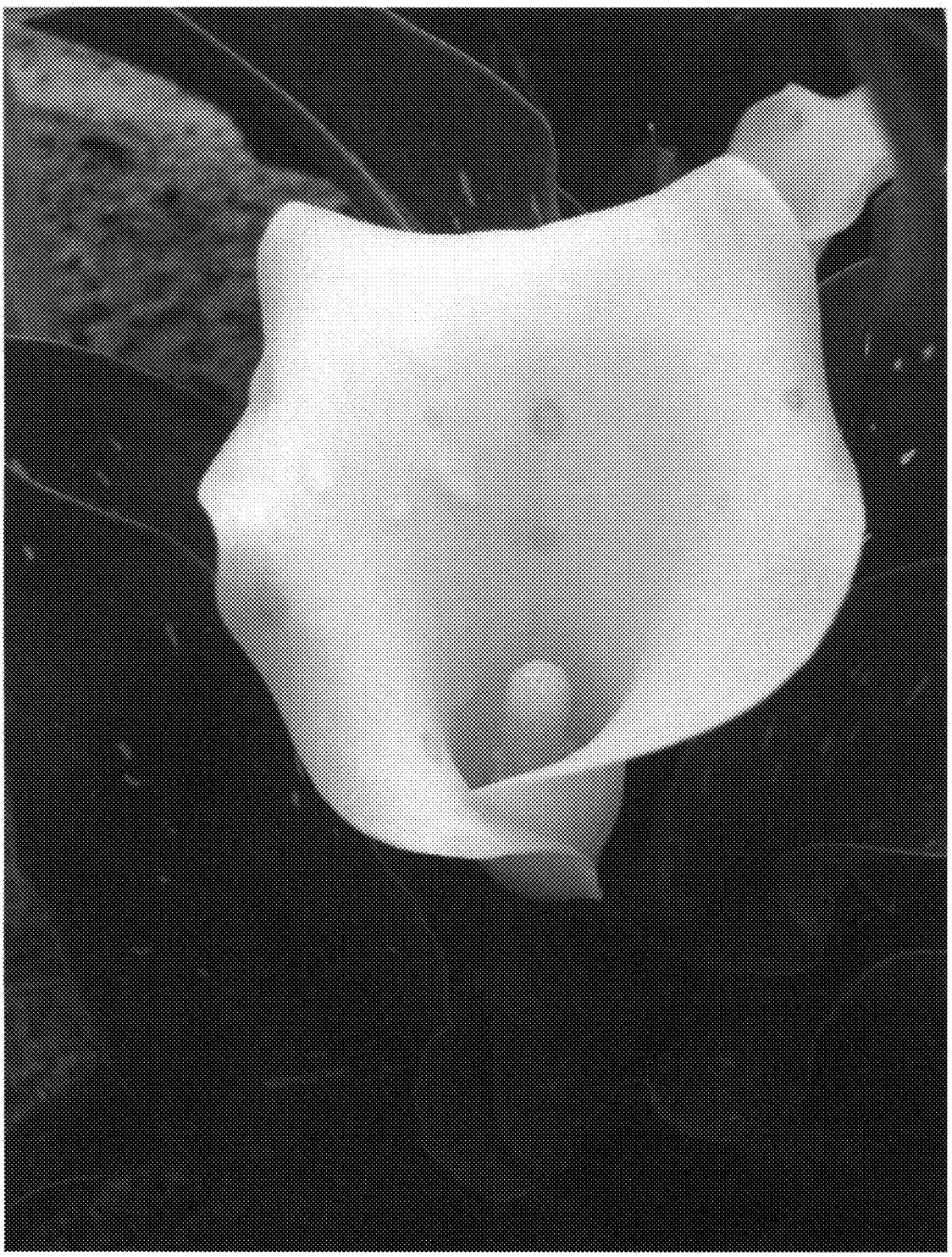
FIG. 3 is a close-up photograph of the new variety.
Figure 4:
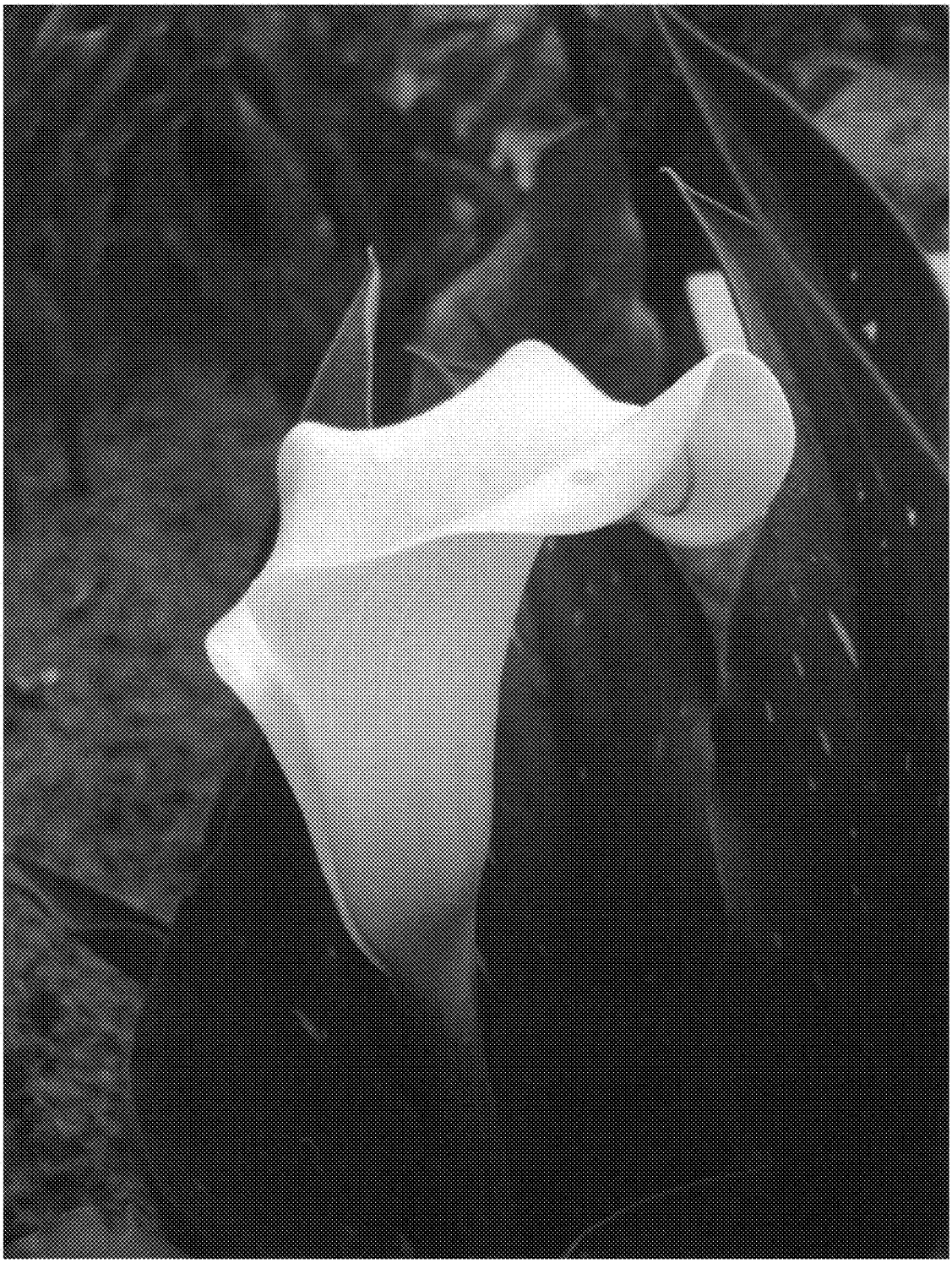
FIG. 4 is a close-up photograph of multiple plants of the new variety.

Size:

*Height of the leaf canopy above the soil.*—18-20 cm.
*Height of top of inflorescence above the soil.*—15-22 cm.
*Diameter.*—10-20 cm.

Form: Erect.
Number of inflorescences per tuber:
*Size* 9-12 cm. in diameter.—3-7 inflorescences.
*Size* 12-15 cm. in diameter.—7-10 inflorescences.
*Size* 15-18 cm. in diameter.—10-15 inflorescences.
Branches:
*Character*.—Many, like the variety 'Odessa' (U.S. Plant Pat. No. 18,833).
*Color*.—Between Yellow-Green Group RHS 146A and 146B.
Leaves:
*Size*.—Width: 3-6 cm. Length: 25-30 cm.
*Number per plant*.—20-30.
*Shape*.—Elliptic.
*Color*.—Upper surface: Green Group RHS 137A to 137B. Lower surface: Green Group RHS 136A to 137B.
*Apex*.—Apiculate.
*Base*.—Attenuate.
*Margin*.—Undulate.
*Veins*.—Configuration: Pinnate. Color: Yellow-Green Group RHS 147A.
*Surface quality*.—Leathery.
*Petiole*.—Length: 5-18 cm. Diameter: 5 mm. Color: Between Yellow-Green Group RHS 144A and 144B.
Roots:
*Color*.—White.
*Branching*.—Similar to other *Zantedeschia* varieties.

The Inflorescence and Seeds

Spathe:
*Size*.—Length: 4-8 cm. Width: 3-6 cm.
*Color*.—Upper surface: Varies between Green-White Group RHS 157A and 157B. Lower surface: Varies between Green-White Group RHS 157A and 157B.
*Vein color*.—Orange-White Group RHS 159C.
*Shape*.—Cupped.
*Apex*.—Acute.
*Base*.—Round.
*Margin*.—Entire.
*Surface texture* (*both surfaces*).—Leathery.
Spadix:
*Size*.—Length: 10-30 mm. Diameter: 2-5 mm.
*Color*.—Between Yellow-Orange Group RHS 16B and 16C.
*Position relative to spathe*.—Upright.
*Shape*.—Elongated.
*Apex*.—Rounded.
Peduncle:
*Size*.—Length: 18-25 cm. Diameter: 3-6 mm.
*Color*.—Upper part is Yellow-Green Group RHS 144A and lower part is Green-White Group RHS 157C.
*Texture*.—Smooth.
Reproductive organs:
*Location of female organs*.—Basal position of the spadix.
*Location of male organs*.—Upper position of the spadix.
*Perianth*.—Conspicuous.
*Stamens*.—Presence: Not visible before pollen release. Number: More than 20. Pollen amount: Similar to 'Picasso' (U.S. Plant Pat. No. 15,282). Color: Between White Group RHS 155A and 155B.
*Anther*.—Shape: Round and wire-like. Length: Less than 1 mm. Color: Between White Group RHS 155A and 155B.
*Filament*.—Length: Less than 1 mm. Color: Between Yellow-Orange Group RHS 16B and 16C.
*Pistil*.—Number: 15 to 30. Length beyond perianth: About 1 mm.
*Stigma*.—Shape: Round. Size: Less than 1 mm.
*Style*.—Length: Less than 1 mm. Color: Between Green-White Group RHS 157A and Yellow-Green Group RHS 145D.
*Ovaries*.—Texture: Smooth. Length: Between 1 to 10 mm. Width: Between 1 to 10 mm. Color: Top color is between Green-White Group RHS 157A and Yellow-Green Group RHS 145D; bottom color is between White Group RHS 155B and Green-White Group 157C.
Seeds:
*Length*.—4-7 mm.
*Width*.—3-6 mm.
*Color*.—Between Yellow-Green Group RHS N144A and 151B.
*Amount*.—Between 1-40.

General

Disease resistance: No unusual susceptibility to diseases noticed to date.
Pest resistance: No unusual susceptibility to pests noticed to date.
Heat tolerance: No heat tolerance.
Hardiness: Not hardy.
Blooming: Tubers planted in a greenhouse in The Netherlands in February produce inflorescences in April. Tubers planted outdoors in The Netherlands in May produce inflorescences in July.
Lastingness: About two weeks on the plant.
Fragrance: None.

I claim:

1. A new and distinct variety of calla lily plant named 'Calgary' as herein described and illustrated.

* * * * *